(12) United States Patent
Marchant (10) Patent No.: US 10,808,192 B2
(45) Date of Patent: Oct. 20, 2020

(54) IDENTIFICATION OF PRODUCTS

(71) Applicant: JOHNSON MATTHEY PUBLIC LIMITED COMPANY, London (GB)

(72) Inventor: Clive Marchant, Cleveland (GB)

(73) Assignee: Johnson Matthey Public Limited Company, London (GB)

(*) Notice: Subject to any disclaimer, the term of this patent is extended or adjusted under 35 U.S.C. 154(b) by 234 days.

(21) Appl. No.: 15/764,098

(22) PCT Filed: Sep. 30, 2016

(86) PCT No.: PCT/EP2016/073490
§ 371 (c)(1),
(2) Date: Mar. 28, 2018

(87) PCT Pub. No.: WO2017/055593
PCT Pub. Date: Apr. 6, 2017

(65) Prior Publication Data
US 2018/0282644 A1    Oct. 4, 2018

(30) Foreign Application Priority Data
Oct. 2, 2015  (GB) .................. 1517474.1

(51) Int. Cl.
| | | |
|---|---|---|
| *C10L 1/00* | (2006.01) | |
| *G01N 33/28* | (2006.01) | |
| *G01N 33/26* | (2006.01) | |

(52) U.S. Cl.
CPC .......... *C10L 1/003* (2013.01); *G01N 33/2882* (2013.01); *C10L 2200/0407* (2013.01);
(Continued)

(58) Field of Classification Search
CPC ....... C10L 1/003; C10L 1/00; G01N 33/2882; G01N 33/2835; G01N 33/28; G01N 33/26
(Continued)

(56) References Cited

U.S. PATENT DOCUMENTS 5,981,283 A * 11/1999 Anderson, II .......... C10L 1/003
                                                      436/27
6,312,958 B1    11/2001 Meyer et al.
(Continued)

FOREIGN PATENT DOCUMENTS

| FR | 3020637 A1 | 11/2015 |
|---|---|---|
| WO | WO2012/153132 A1 | 11/2012 |
| WO | WO2014/081556 A1 | 5/2014 |
| WO | WO2014/179646 A1 | 11/2014 |

OTHER PUBLICATIONS

PCT/EP2016/073490, International Search Report dated Jan. 23, 2017.
(Continued)

*Primary Examiner* — Christine T Mui
(74) *Attorney, Agent, or Firm* — BakerHostetler (57) ABSTRACT

A marking method which is a method of marking a product having a distillation range is disclosed. The method comprises the step of adding to said product a first marker, a second marker and optionally one or more further markers. Each marker has a distillation range including a minimum boiling point (Min BP), a maximum boiling point (Max BP) and a maximum distillation boiling point (Max DBP) which is the temperature at which the maximum volume of the marker distils. Each marker has a different distillation range from each other marker and at least one marker has a Max DBP which is within the distillation range of the product.
(Continued)

The first marker has a distillation range in the marked product which extends over the whole of the product distillation range.

15 Claims, 5 Drawing Sheets

(52) U.S. Cl.
CPC ... *C10L 2200/0469* (2013.01); *C10L 2230/16* (2013.01); *C10L 2290/543* (2013.01); *C10L 2290/60* (2013.01)

(58) Field of Classification Search
USPC .......................................................... 436/56
See application file for complete search history.

(56) References Cited

U.S. PATENT DOCUMENTS

2004/0147413 A1　7/2004　Spall et al.
2014/0134746 A1* 5/2014　Green .................... C10L 1/003
　　　　　　　　　　　　　　　　　436/127

OTHER PUBLICATIONS

PCT/EP2016/073490, Written Opinion dated Jan. 23, 2017.
GB 1616639, Combined Search and Examination Under Sections 17 and 18(3) Report dated Mar. 16, 2017.
GB 1517474, UK Search Report dated Mar. 24, 2016.

* cited by examiner

Figure 7: Calibration Process

Figure 8: Sample Analysis Process.

IDENTIFICATION OF PRODUCTS

CROSS-REFERENCE TO RELATED APPLICATIONS

This application is the National Stage of International Patent Application No. PCT/EP2016/073490 filed Sep. 30, 2016, which claims priority from Great Britain Patent Application No. 1517474.1, filed Oct. 2, 2015, the disclosures of each of which are incorporated herein by reference in their entireties for any and all purposes.

This invention concerns a method and systems for marking products such as fuels in which the marking is detectable following further distillation of the marked products.

It is already common to mark products with tags, tracers or markers for the purposes of identifying products and to assist in distinguishing original products from fake or adulterated products. As an example, the marking of hydrocarbon fuels has been carried out in many countries for various purposes, including operational reasons, e.g. to assist in distinguishing one grade of fuel from another, or for other reasons, in particular to ensure fuel quality, deter and detect adulteration and to provide a means to check that the correct tax has been paid. It is therefore well known to add tracers to hydrocarbon liquids such as fuels. A typical application is the tagging of hydrocarbon fuels in order to identify the liquid at a subsequent point in the supply chain. Apart from fuels, other products, such as vegetable oils may be marked to identify the product produced at a particular source, or certified to a particular standard.

A problem associated with marking hydrocarbon fuels is that they typically consist of a large number of different organic compounds which have a range of boiling points. A typical fuel comprises a distillation cut, i.e. a range of compounds which are produced from distilling petroleum between specified upper and lower temperature limits. Diesel fuel, for example is the distillation cut taken between 200 and 350° C. If diesel fuel is marked with a marker, it may be possible to remove the marker by distilling the marked fuel to remove the marker (or to distil the lower-boiling fuel compounds away from the higher boiling residue containing the marker) and thereby defeat the identification system used. Even if a marker has a wide boiling range covering most or all of the boiling range of the distillation product, distillation of the marked product will result in fractions containing different concentrations of marker. If a distilled product is then diluted with an unmarked product, the concentration of the marker in the total product is changed again, thus making accurate quantification of the marked product in unmarked product impossible. It has been previously proposed that fuels may be marked with more than one marker in order to produce a unique code from the identity and quantity of markers found in a product. In the case where a fuel product is distilled after the marker codes have been added, such a code would be lost if the boiling and distillation behaviour of each marker is different, leading to a different marker code in the distilled product from that present in the original product.

WO2012/153,132 and WO2014/081,556 describe methods of marking fuels.

One object of the invention is to provide a method of marking distillation product, such as hydrocarbon fuels, which overcomes at least some of the problems associated with the methods of the prior art.

According to the invention, we provide a marking method which is a method of marking a product having a distillation range comprising the step of adding to said product a first marker, a second marker and optionally one or more further markers, each marker having a distillation range including a minimum boiling point (Min BP), a maximum boiling point (Max BP) and maximum distillation boiling point (Max DBP) which is the temperature at which the maximum volume of the marker distils, each marker having a different distillation range from each other marker and at least one marker having a Max DBP which is within the distillation range of the product, characterised in that the first marker has a distillation range in the marked product which extends over the whole of the product distillation range.

Figure 1:
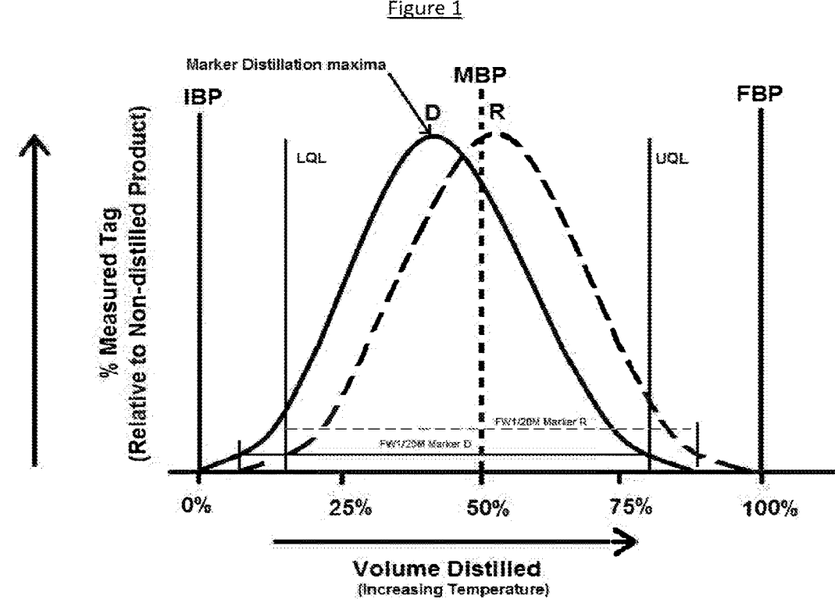
FIG. 1: A schematic distillation profile of a distillable product containing markers D and R.

The markers have a distillation profile in the product which typically follows a curve when plotted on a distillation profile of temperature vs concentration of the marker in the distillate. FIG. 1 is a diagram which shows a typical such curve.

Terminology used in this patent application is defined as follows:

"Distillation range" is the range of temperatures over which a distilled mixture or a component thereof is distilled from a distillation feedstock.

"Product distillation range" is the distillation range of the product which is marked using the method of the invention.

"Marker distillation range" is the distillation range of any one marker in the product which is marked using the method of the invention.

"First marker distillation range", second marker distillation range, nth marker distillation range, "Marker A distillation range" etc respectively refer to the marker distillation range of the first, second, nth marker, or "Marker A" and similar terms should be interpreted in a similar way, mutatis mutandis.

"Minimum boiling point" (Min BP), "Maximum boiling point" (Max BP) are the minimum and maximum temperatures of a marker distillation range.

"Maximum distillation boiling point" (Max DBP) which is the temperature at which the maximum volume of a marker is distilled, being the temperature at which the distillation profile of temperature vs concentration of marker in the distillate passes through a maximum.

"Initial Boiling Point" (IBP) is the temperature at which the first drop of distillate appears after commencement of distillation.

"Final Boiling Point" (FBP) is the maximum temperature observed when distillate is no longer recovered.

"Mid Boiling Point" (MBP) is the temperature at which the volume of distillate is fifty percent of the initial volume; sometimes referred as the 50:50 Point.

"Distillate" is the liquid that results from the condensing of vapour produced by heating a source liquid. It is the product recovered by distillation when heated from the IBP to the final distillation temperature.

"Residue" is liquid that remains after distillate volume has been removed by heating. It is the volume of product that remains from the final distillation temperature to the FBP.

"Quantification Range" is the distillation range of the product within which the method of the invention may provide a quantitative measure of the proportion of the marked product found in a measured sample of an unknown product. The quantification range of the product may cover the same temperature range as the product distillation range, i.e. it may extend between IBP and FBP, or it may extend between a narrower range of temperatures than the product distillation range.

FW$\frac{1}{20}$M is the Full Width one twentieth Max height of a marker distillation profile. The FW$\frac{1}{20}$M is shown in FIG. 1. The FW$\frac{1}{20}$M is the full width of the distillation profile curve } of a marker at 5% height (i.e. 5% of the curve maximum along the marker concentration axis).

Preferably each marker has a Max DBP which is within the distillation range of the product. It is preferred that the Max DBPs of the first, second and each further marker are distinct from each other and distributed over a major portion of the product distillation range. It is further preferred that if the number of markers added to the product is n then the Max DBP of each marker falls within a unique 1/n distillate fraction of product which is being marked. For example if four different markers are added to a product having a distillation range defined by an initial boiling point (IBP) and a final point such that 100% of the product is distilled between IBP and FBP, then the first marker Max DBP may lie within the temperature range between the IBP and the temperature at which 25% of the distillate fraction is collected, the second marker Max DBP may lie within the temperature range within which the next 25% of the distillate fraction is collected, and so on. Selecting the markers so that their Max DBP temperatures are distributed across the distillation range in this way ensures that it is likely that distillation of a portion of the product which has been so marked would result in the distilled portion containing one or more of the added markers so that it could be identified as a material which has been derived from the original product. In that case detection of more than one marker may further assist the identification.

In a preferred embodiment, the marker distillation ranges of at least two markers overlap each other, whilst their respective max DBPs are different. When marker distillation ranges overlap each other, a distillation fraction including the distillation range in which the marker distillation ranges overlap includes both or all of the respective markers in the ratio which is distinctive for the particular distillation fraction which has been collected. If that distillation fraction is then diluted with an unmarked sample or a sample containing different markers, the original markers which were added during the marking method remain present in the distillation fraction in the same distinctive ratio. Analysis of a sample of the diluted distillate would then reveal that the sample contained a portion of the original marked product, the distillation range of the marked product which is in the sample and the amount of dilution which has occurred.

In a particularly preferred embodiment of the invention, at least one marker has a wide marker distillation range in the marked product. This type of marker may be referred to hereinafter as a "Wide Marker". A wide marker may have a distillation range extending over the whole of the product distillation range. A wide marker may have a FW½₀M extending from the IBP to the FBP. Alternatively, a wide marker may have a distillation range extending over a portion of the product distillation range. The portion of the distillation range over which the wide marker distillation range extends may be the temperature range over which at least 50% of the distillate fraction volume distils. The portion of the distillation range over which the wide marker distillation range extends may be the temperature range over which at least 50% of the distillation residue volume remains. It is preferred that at least one marker has a marker distillation range which extends to a lower temperature than the IBP and/or which extends to a higher temperature than the FBP. In this way either any distillate portion or any residue portion or both a distillate and a residue portion contain at least some of the at least one marker.

In one form of this embodiment the first marker is a wide marker whilst the second marker is not a wide marker but has a marker distillation range which overlaps the marker distillation range of the first marker and overlaps the IBP of the product. In this form of the method, any distillate fraction distilled from the distilled product always contains a portion of the first marker and the second marker. The ratio of the concentration (or amounts) of the first and second markers indicates which distillate fraction is contained within the sample that is analysed. In another form of this embodiment the first marker is a wide marker whilst the second marker is not a wide marker but has a marker distillation range which overlaps the marker distillation range of the first marker and overlaps the FBP of the product. In this form of the method, any residue fraction derived from the distilled product always contains a portion of the first marker and the second marker. The ratio of the concentration (or amounts) of the first and second markers indicates which residue fraction is contained within the sample that is analysed. In another form of this embodiment, the first marker is a wide marker whilst the second marker is not a wide marker but has a marker distillation range which overlaps the marker distillation range of the first marker and overlaps the FBP of the product and a third marker is present which is not a wide marker but has a marker distillation range which overlaps the marker distillation range of the first marker and overlaps the IBP of the product. In this form of the method, any fraction derived from the distilled product always contains a portion of the first marker and of either the second marker or the third marker. This enables a sample of the product to be identified from the presence of at least the first marker, the identification of the second or third markers denotes whether a distillate or a residue fraction of the product is present in the sample and the ratio of the markers may be used to determine which distillate fraction is present.

At least two markers may be wide markers. In this embodiment at least two markers may have a distillation range extending over the whole of the product distillation range. In this case the Max DBP of each of the at least two wide markers are different. The Max DBP of each of the at least two wide markers may differ by from 1 to 100° C., more preferably 5-50° C. The Max DBP of each of the at least two wide markers may differ by from 5 to 30° C. The Max DBP of any one marker may lie within a temperature range which is the temperature mid-point of the product distillation range +/−10% of the product distillation range. The Max DBP of each marker may lie within a temperature range which is the temperature mid-point of the product distillation range +/−10% of the product distillation range. In a particular embodiment of the invention, at least two markers are wide markers and each of said wide markers has a Max DBP within a temperature range which is the temperature mid-point of the product distillation range +/−10% of the product distillation range. When the Max DBP of each of the at least two wide markers are different, the amount of each of the markers in any distillate or residue derived from the marked product will be different and their concentration ratio may be used to calculate the distillate fraction they represent. At least two markers may have a distillation range extending over a portion of the product distillation range, at least one marker distillation range (e.g. the distillation range of the first marker) extending to a lower temperature than the IBP and at least one marker distillation range (e.g. the distillation range of the second marker) which extends to a higher temperature than the FBP. In this case it is preferred that the distillation ranges of these markers overlap in the portion of the distillation range between the IBP and the FBP. In this way it is possible to distinguish and identify any distillate or residue fraction by identifying the ratio of the concentration, or response, of the markers. Response as used in this context means the response of the markers to an analytical method. The response may be used to calculate the ratio between two or more markers, whether or not the concentration of each marker is calculated.

It may be beneficial commercially to use a minimum number of markers in the system and method of the invention. Apart from the cost of the markers themselves, the addition of many markers takes more time than the addition of fewer markers and may involve more complex and costly equipment for metering the correct amount of each marker into the product. The analysis and quantification of a larger number of markers is likewise more complex and time consuming than the analysis of fewer markers. For these reasons the number of markers added to the product may be no more than four, especially no more than three and preferably no more than two. If only two markers are used then, in the preferred embodiment, both the first marker and the second marker are wide markers.

The marking method of the invention provides the opportunity to quantify the proportion of a marked original product which is identified in a sample of an "unknown" material. The product distillation range of the original marked product over which the method may be quantitative may be referred to as the quantification range. The quantification range of the product may cover the same temperature range as the product distillation range, i.e. it may extend between IBP and FBP, or it may extend between a narrower range of temperatures than the product distillation range. The quantification range depends on the degree of overlap of the marker distillation ranges with the product distillation range. The quantification range may depend on the degree of overlap of each marker distillation range with each other marker distillation range. Generally, the method of the invention may be quantitative over a distillation range which overlaps at least two marker distillation ranges. That is, when a distilled sample contains two markers, their presence, identity and relative amounts may be used to estimate the quantity of distilled product in the sample.

The quantification range may be defined by a lower quantification lower limit (LQL) at its lowest distillation temperature and a quantification upper limit (UQL) at its highest distillation temperature. It is preferred that the LQL is the lowest temperature of the $FW\frac{1}{20}M$ of the marker distillation profile of the second-lowest boiling marker. It is preferred that the UQL is the highest temperature of the $FW\frac{1}{20}M$ of the marker distillation profile of the second-highest boiling marker. Therefore, in one embodiment, the method of the invention may be quantitative between the lowest temperature of the $FW\frac{1}{20}M$ of the marker distillation profile of the second-lowest boiling marker and the highest temperature of the $FW\frac{1}{20}M$ of the marker distillation profile of the second-highest boiling marker. Thus advantageously the LQL is the lowest distillation temperature at which a ratio can be measured and the UQL is the highest distillation temperature at which a ratio can be maintained. Most preferably the LQL is at or below the IBP and the UQL is at or above the FBP. However, in some embodiments that may not be the case without reducing the utility of the invention. That is because, even in that case, there may not be a cost effective volume of product that could be distilled outside of the quantification range.

The product is a distillable product. The product may itself be a distilled product, such as a distilled fraction of petroleum. The product may comprise or consist of a hydrocarbon liquid. The hydrocarbon liquid may comprise more than one hydrocarbon compound, i.e. it may comprise a mixed hydrocarbon. In some embodiments, the hydrocarbon liquid contains a mixture of different hydrocarbon compounds. The hydrocarbon liquid may be derived from petroleum or a biomass source. The hydrocarbon liquid may be for use as a fuel or a solvent.

The hydrocarbon liquid may comprise a diesel fuel, gasoline, kerosene or any other hydrocarbon liquid. Fuels typically contain additives such as surfactants and other chemicals. The marker may be selected to be distinguishable from such additives.

The markers are capable of being detected and quantified within the quantification range of the product. Therefore, the nature of the markers and the amount added to the product must enable their subsequent detection by a suitable analytical method. The amount of each marker added is preferably calculated to provide the concentration of the marker greater than the lowest limit of quantification (LLQ). The LLQ may be the concentration at which a given minimum level of certainty can be guaranteed in the measurement of the concentration of the marker. The method of detection or analysis used may be selected from those which have the required sensitivity and selectivity according to the type of marker to be detected. Optical methods such as fluorescence, infra-red or UV spectroscopy may be used in some cases, although we have found that the variable nature of hydrocarbon products may make quantitative detection of a marker by optical methods unreliable. The markers may be detectable by mass spectrometry, or by a separation method such as chromatography (including gas chromatography, liquid chromatography, HPLC) or electrophoresis in combination with an identification method which may be selected from any suitable method such as flame ionisation detection, mass spectrometry or electron capture detection. In preferred embodiments, the analytical method is capable of providing a response which is proportional to the quantity of marker found in the sample The markers are selected to be distillable when mixed with the product to be marked. Suitable markers are miscible with the distilled product which is to be marked. For marking of hydrocarbons each marker is suitably an organic compound having a boiling point within the distillation range of the distilled product to be marked and distillation range characteristics selected as described above. The markers may be aromatic compounds, having substituents selected from halogens, alkyl groups, aromatic groups, nitro groups, ethers (such as biphenyl ethers for example) or amines. Alkyl or aromatic substituents may be further substituted, optionally by halogens nitro groups, ethers or amines. Preferred halogen substituents are fluorine-containing. Examples of suitable distillable markers for marking hydrocarbon liquids may be found in WO2012/153132.

The response of a marker to a particular detection or analysis method may vary across a distillation range due to the change of the composition of the distilled product, i.e. the matrix in which the marker is dispersed. This matrix effect may affect the usefulness of a calibration if the calibration has been carried out at a particular matrix composition or even in a different matrix. This may be overcome by applying a correction factor, if available, or by using an internal standard. An internal standard may comprise an isotopically altered version of one of the markers. Alternatively, an internal standard may be a compound which is similar to one of the marker compounds but which has a minor change, for example a small change of an organic substituent group or an isomer of a marker compound.

We further provide an identification method which is a method of identifying a known marked product in an unknown sample, said known marked product being a product which has been marked by the marking method of the invention, comprising the step of analysing said sample to identify whether said first marker, said second marker or a said further marker is present.

When the first, second or further markers are found in the unknown sample then the method may further comprise the steps of calculating the response ratio of the first, second and further markers, if present, to each other.

The response of any of the markers found in the unknown sample may be compared with the response of the same marker in a reference sample. The response ratio(s) of any of the markers to any of the other markers found in the sample may be compared with the response ratio(s) of the same marker in a reference sample. In preferred embodiments, the reference sample represents the known marked product containing a known concentration of said marker. The reference sample may be a sample known to have been taken from the original known marked product after it has been marked using the method of the invention. Alternatively, the reference sample may be a sample made for the purpose of reference, such as a standard sample, which, preferably has been prepared to provide a response to the analytical method which is similar to the response which is or would be provided by the known marked product. Alternatively, the response of the markers (or the response ratio(s) of any of the markers) found in the unknown sample may be compared with a stored response (or response ratio), for example a reference spectrum, which has been generated previously and stored. The stored response may comprise a full spectrum or may comprise a set of response values. The reference response may be stored, accessed and compared electronically.

If the response ratio of the markers in the unknown sample is found to be the same (within error) as the response ratio of the same markers in the reference sample, then it may be inferred that the unknown sample contains an un-distilled sample of the marked product. That is because distillation of the marked product changes the relative amounts of the markers in the distillate and residue. "The same (within error)" may be taken to have the usual meaning for an analytical test based on the nature of the error inherent in the analysis. In some embodiments, the response or response ratio may be taken to be the same (within error) if the responses are within +/−10%. Therefore, if the response ratio calculated for the markers found in the unknown sample is in the range 0.9 to 1.1 times the response ratio of the same markers in the known reference sample then it may be inferred that the unknown sample contains an undistilled sample of the marked product.

If the markers are present and the response ratio of the markers is different from the response ratio of the same markers in a reference sample, then it is likely that the sample contains a distilled fraction of the marked distilled product. Consideration of the change in the response ratio of the markers may then indicate whether the distilled fraction is a distillate fraction or a residue fraction. The presence of a marker having a distillation range overlapping the FBP of the product but which does not also overlap the IBP of the product would indicate that the sample contains a distillation residue fraction of the original marked product. The presence of a marker having a distillation range overlapping the IBP of the product but which does not also overlap the FBP of the product would indicate that the sample contains a distillate fraction of the original marked product. Therefor the identification method of the invention may further comprise the step of determining whether the sample contains the marked product or a fraction thereof. This determination may be made by comparing the response ratio of at least some of the markers found in the sample with the response ratio of at least some of the markers in a reference sample. The method may further comprise determining from the comparison of the response ratio of at least some of the markers found in the sample with the response ratio of at least some of the markers in a reference sample which fraction of the marked product is present in the unknown sample. When the first marker has a lower maximum distillation boiling point (max DBP) than the max DBP of said second marker and the response ratio of the first marker to the second marker in the unknown sample is greater than the response ratio of the first marker to the second marker in the reference sample, it can be inferred that the unknown sample contains a distillate fraction of the marked product. When the first marker has a lower maximum distillation boiling point (max DBP) than the max DBP of said second marker and the response ratio of the first marker to the second marker in the unknown sample is less than the response ratio of the first marker to the second marker in the reference sample, it can be inferred that the unknown sample contains a residue fraction of the marked product.

When the comparison of the response ratio of at least some of the markers found in the sample with the response ratio of the same markers in a reference sample has been made, the fraction of the marked product (e.g. a distillate fraction or a residue fraction) in the sample may be identified. In order to determine whether dilution of the product has occurred, a correction factor may be used. The correction factor may be calculated by calculating the concentration of markers which would be present in an undiluted sample of the distillate fraction corresponding to the marker ratio found in the sample. The correction factor may be a multiplier required to convert the concentration of the marker to 100%. This factor may then be used as a comparator, or calibration of the markers in the product, from which dilution of the distillate fraction may be estimated.

Particular embodiments of the identification method of the invention may include a calibration step. The calibration step provides information about the marked product which is a mixture of the first and second markers with the original product (e.g. diesel or other hydrocarbon fuel). The calibration may be carried out on a sample of known marked product or using a reference sample prepared for the purpose of calibration. A calibration method is shown schematically in FIG. 7. In the calibration method shown in FIG. 7, a reference sample containing known concentrations of first marker (A) and second marker (B) is analysed (step 10) by a method providing a response which is proportional to the concentration of the markers in the sample. This step may be omitted if the marker concentration is already known. However, it is usually advisable to carry out this step to check the concentration or to provide or confirm the response of each marker in the product. The ratio of the concentration, or response, of the markers in the reference sample is calculated in step 12. The reference sample is then distilled (14) incrementally to yield measured cumulative volumes of distillate and residue which are then analysed (16) to determine the concentration or response of the markers in each volume of residue and distillate. The concentrations or analytical responses of the markers may be plotted vs distillate (or residue) volume and interpolated. The ratio of response NB is calculated (18) for each cumulative volume and may be plotted and interpolated (24). Correction factors may then be determined (20A, 20B) for each marker in each of the distillate and residue volumes as described hereinafter.

Figure 7:
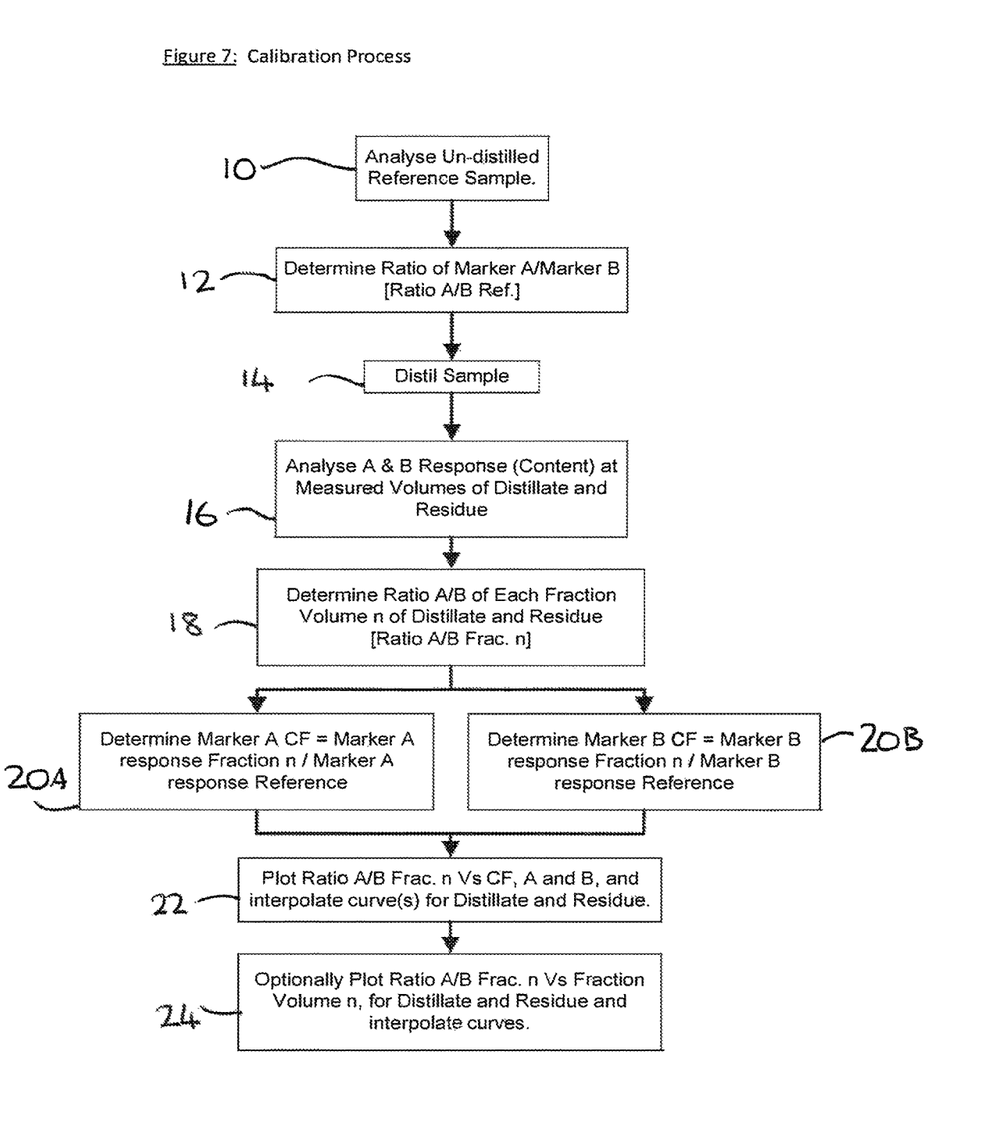
FIG. 7: Process diagram for calibration method

The correction factors may be plotted vs the NB response ratio (22) and interpolated using a suitable curve-fitting method (e.g. a polynomial function). As a result of the calibration method, any distillate or residue fraction of the known marked product, and its volume, may be identified in an unknown sample of a product.

In preferred embodiments, the correction factor for a particular marker, which may be the first or second marker, is calculated by a method comprising the steps of:
  a) distilling a reference sample representing the known marked product containing a known concentration of the particular marker to obtain at least two reference distillate fractions each of known distillation volume % and at least two reference residue fractions each of known residue volume %;
  b) analysing each of said distillate and residue fractions to determine the response of the particular marker in each fraction;
  c) determining the correction factor (CF) for the particular marker in each fraction from:

$$CF = \frac{\text{response of the particular marker in fraction}}{\text{response of the particular marker in reference sample}}$$

Thus, a correction factor for each of the first and second markers in the product may be calculated for the known marked product. When the correction factor is known across a range of distillate fractions, it may be used to calculate the proportion of a distillate or residue fraction of a known marked product which has been incorporated into an unknown product.

Comparison of the response ratios of at least two markers in the unknown sample with the response ratios of the same markers in the reference can provide information as to the dilution of the distilled product. If the response ratio of the markers in the unknown sample is found to be the same (within error) as the response ratio of the same markers in the reference sample, but the response of the marker in the unknown sample is less than the response of the same marker in the known reference sample, then it may be inferred that the sample contains a diluted version of the marked distilled product.

Therefore, the method of the invention may further comprise the step of comparing the response ratios of at least two markers in the unknown sample with the response ratios of the same markers in the reference in order to determine if the unknown sample contains the marked distilled product or a fraction thereof which has been diluted. Thus the method of the invention may comprise using the response ratios of at least two markers in the unknown sample to determine if the unknown sample contains the marked product, or a fraction (distillate or residue) thereof. The method of the invention may further comprise using the response of at least a marker in the unknown sample to determine the dilution level of the marked product or the fraction thereof. The method of the invention therefore provides the possibility to identify a marked product and also a distilled fraction of a marked product even after dilution.

Figure 8:
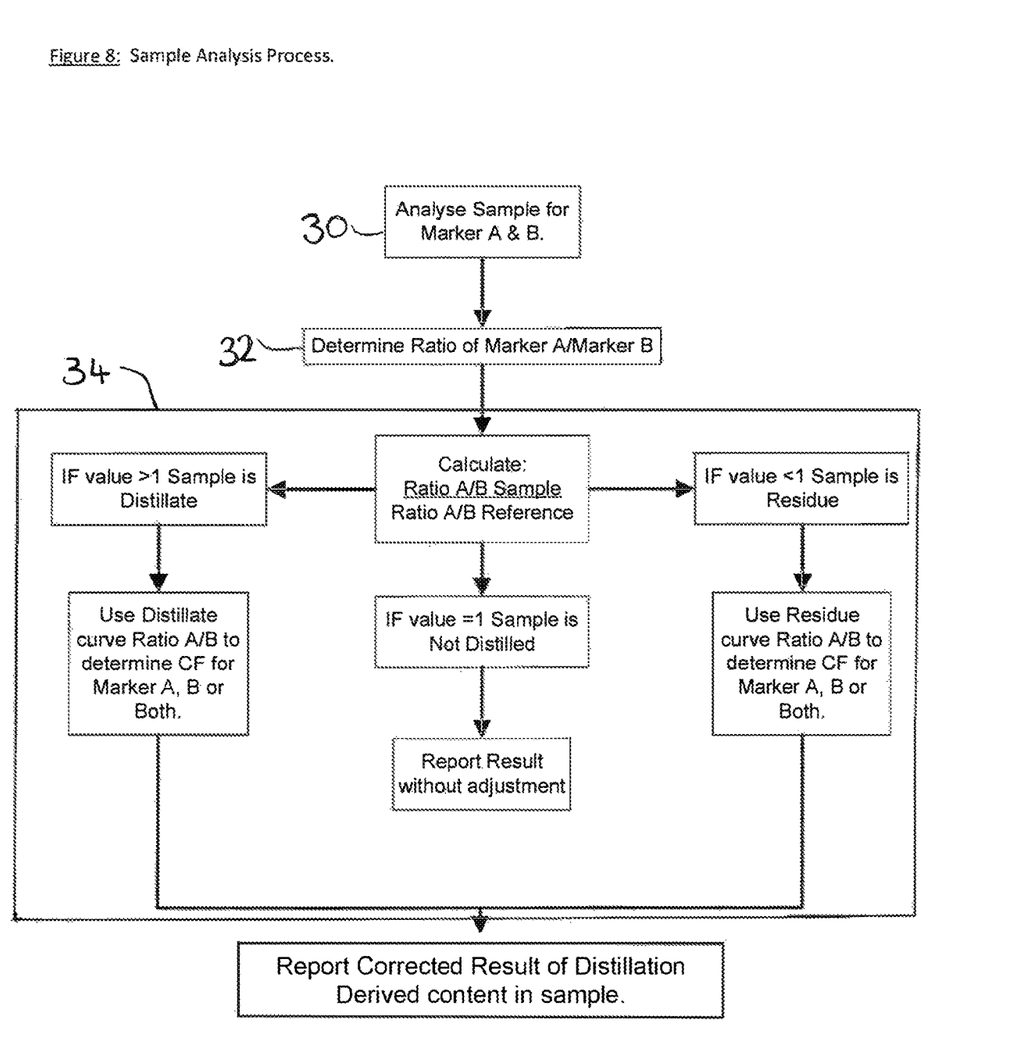
FIG. 8: Process diagram for sample analysis method

A method for analysing and determining the origin of an unknown sample is shown schematically in FIG. 8. The sample of unknown product is first analysed (step 30 in FIG. 8) to determine the concentration or response of each of the first marker (A) and second marker (B) and the ratio NB is calculated (32). The ratio NB is used in step 34 to determine the fraction of known marked product which may be contained in the unknown sample. If the ratio NB in the unknown sample is the same as that found in the reference sample (step 12 of FIG. 7) i.e. ratio NB (sample)/ratio NB (reference)=1, then the unknown sample may be inferred to contain an undistilled portion of the known marked product to which the reference refers. If the ratio NB (sample)/ratio NB (reference)<>1 then it may be inferred that the unknown sample contains a distilled fraction of the known marked product. If the ratio NB (sample)/ratio NB (reference)>1 then, provided marker A has a lower maximum distillation boiling point (max DBP) than marker B, the unknown sample contains a distillate fraction. If the ratio NB (sample)/ratio NB (reference)>1 then, provided marker A has a lower maximum distillation boiling point (max DBP) than marker B, the unknown sample contains a residue fraction. Comparison with the appropriate correction factor vs NB ratio curve then provides the correction factor which is used to calculate the volume fraction of the marked product in the unknown sample.

The invention is described herein with reference to the accompanying drawings, which are.

The method of the invention will be further described in the following examples.

EXAMPLE 1

A diesel fuel was marked with two markers (Tag A and Tag B) at a marker concentration of each marker of 1 ppm to form a marked mixed hydrocarbon product. The ratio of Tag A to Tag B was 1:1. The marked mixed hydrocarbon was then used to calibrate the measurement device so that identification and quantification of the markers can be made in any mixed hydrocarbon matrix.

Figure 2:
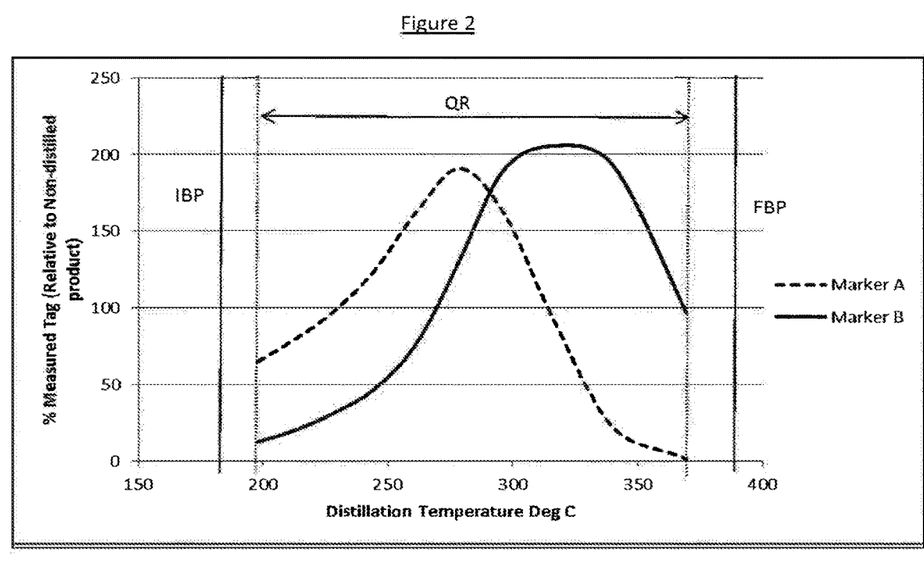
FIG. 2: distillation profile of diesel fuel containing markers A and B used in Example 1.

Distillation profiles of Tag A and Tag B within the mixed hydrocarbon were determined using a modified ASTM D-86 protocol. 10% by volume fractions were collected and measured for marker content. The analytical method used for the markers was gas chromatography—mass spectrometry using single ion monitoring. Deuterated versions of Tag A and Tag B were used as internal standards. Distillation curves were created from the values in Table 1 and these are shown in FIG. 2 for each marker.

TABLE 1

| Distillation Temp (° C.) | % Tag A | % Tag B | Equivalent Distillate Volume Point (%) |
|---|---|---|---|
| 197.8 | 64.94 | 12.74 | 10 |
| 212.2 | 79.05 | 20.04 | 20 |
| 228.0 | 97.32 | 31.35 | 30 |
| 244.6 | 124.3 | 47.32 | 40 |
| 261.4 | 162.72 | 77.14 | 50 |
| 278.5 | 191.03 | 130.29 | 60 |

TABLE 1-continued

| Distillation Temp (° C.) | % Tag A | % Tag B | Equivalent Distillate Volume Point (%) |
|---|---|---|---|
| 296.2 | 162.4 | 189.59 | 70 |
| 315.8 | 94.07 | 205.6 | 80 |
| 339.9 | 22.73 | 193.29 | 90 |
| 369.6 | 1.41 | 96.59 | 100 |

It may be advantageous to have a larger number of data points and so distillation volumes smaller than 10% by volume may be preferred. The distillate fractions where there is only a single marker can be determined from these curves and so a quantification range QR may be established, as shown in FIG. 2 between the vertical dotted lines.

Figure 3:
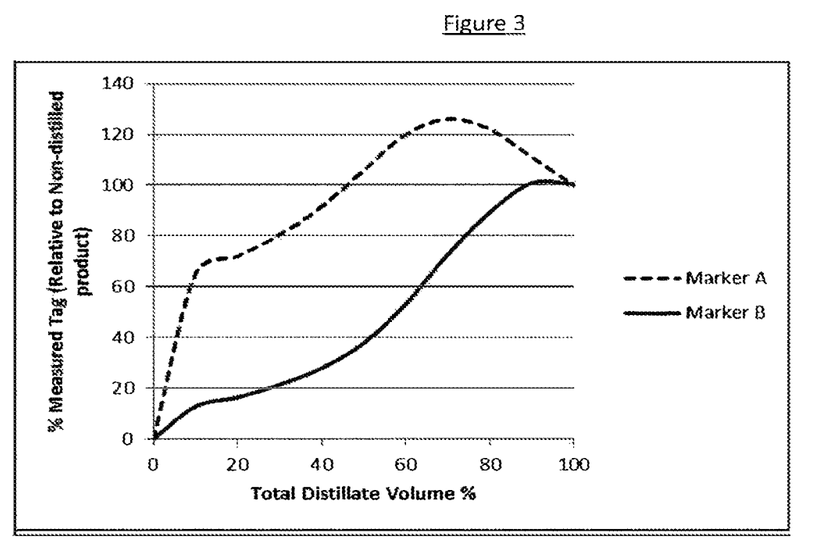
FIG. 3: marker concentration vs distillate volume for markers A and B from Example 1.

The volume of marker measured in each known total volume of distillate was measured and tabulated in Table 2. The volume of marker measured in each known total volume of distillation residue, was measured and tabulated in Table 3. A table for each of the 'Distillate' and the distillation 'Residue' was created separately because they may be deemed as separate products for future quantification. In Tables 2 and 3, the percent marker was calculated relative to the originally marked diesel. Once fully distilled the distillation curves for each marker were produced and are shown in FIG. 3. Note, these curves detail the marker content in the bulk distillate volume, and not the marker content at each distillate fraction as shown in FIG. 2.

Figure 4:
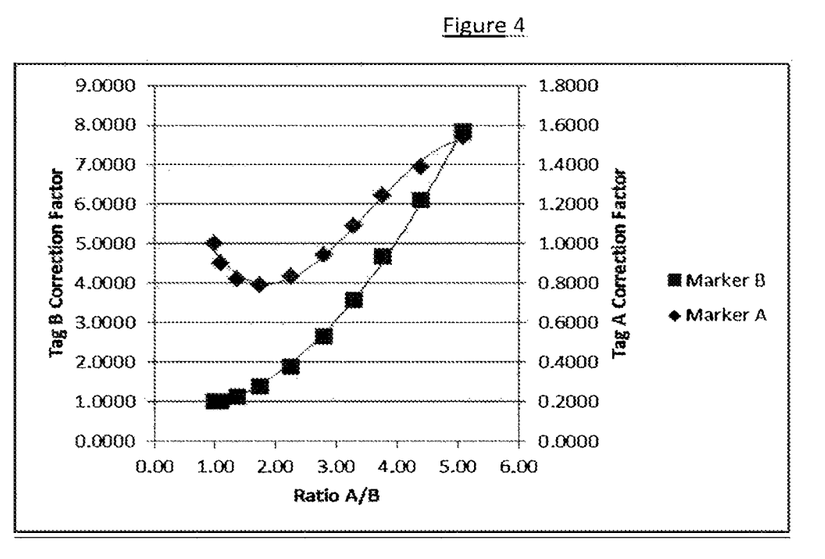
FIG. 4: plot of marker ratio vs correction factor for markers A and B in distillate from Example 1.

At each measured volume the ratio of marker A to marker B was also determined and recorded. It can be seen from the data above, in Table 2, that the ratio of the two markers can be used to determine the final distillation temperature achieved and total distillate volume obtained in any fraction of the original marked diesel. An ideal tracer would measure 100% marker relative to the original marked diesel since it is derived from the same marked product and so is a portion of the marked product. However, it can be seen that the marker content is either deficient in relative content or in excess of the relative content, therefore a correction factor may be made to account for this. Correction factors for each marker were calculated and tabulated as seen in Table 2 above. It can now be seen that we can assign a correction factor, for each marker, across the distillation range of the marked diesel. The correction factors for each of marker A and marker B were plotted in FIG. 4 and interpolated using a polynomial fit to produce a curve for each marker in the distillate. Using the marker ratio we can determine, from the relevant curve, the position of the final distillation point and thus the distillate volume, and thus we can determine the correction factors to be made to the marker content at this distillation volume. Thus by creating a marker ratio to correction factor curve as shown in FIGS. 4 and 6 we can now determine the correction factor at any distillation point by use of either a curve fit or curve spline.

Figure 5:
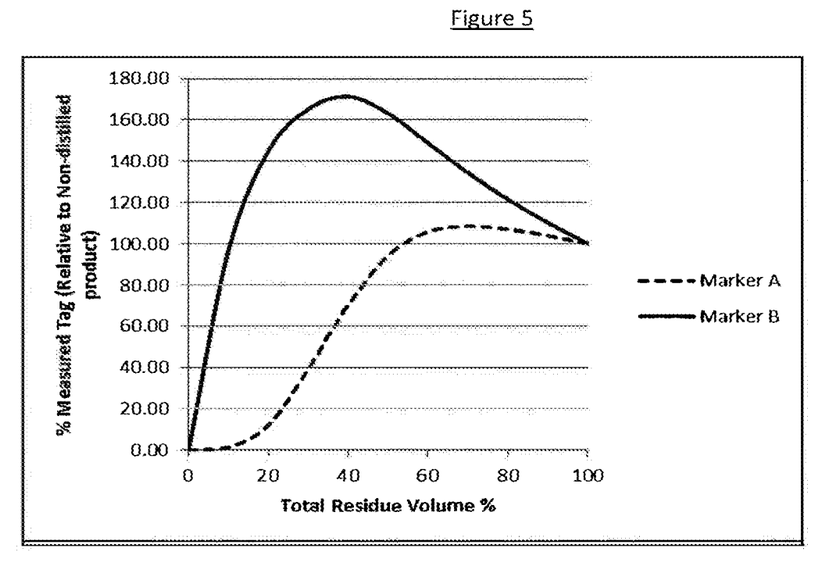
FIG. 5: marker concentration vs residue volume for markers A and B from Example 1.
Figure 6:
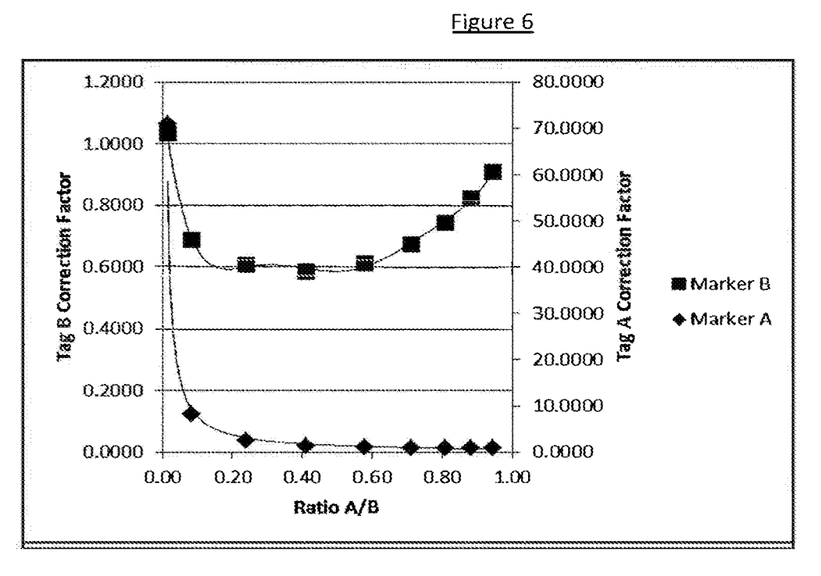
FIG. 6: plot of marker ratio vs correction factor for markers A and B in residue from Example 1.

Similar marker concentration curves and correction factor curves were made for the distillation residue and these are shown in FIGS. 5 and 6.

TABLE 2

Distillate

| Total Distilled Volume % | % Marker A | Marker A ppm | % Marker B | Marker B ppm | Ratio A/B | Marker A Correction Factor | Marker B Correction Factor |
|---|---|---|---|---|---|---|---|
| 0 | 0 | 0.00 | 0 | 0.00 | 0 | 0 | 0 |
| 10 | 64.94 | 0.65 | 12.74 | 0.13 | 5.0973 | 1.5399 | 7.8493 |
| 20 | 72.00 | 0.72 | 16.39 | 0.16 | 4.3926 | 1.3890 | 6.1013 |
| 30 | 80.44 | 0.80 | 21.38 | 0.21 | 3.7628 | 1.2432 | 4.6780 |
| 40 | 91.40 | 0.91 | 27.86 | 0.28 | 3.2805 | 1.0941 | 3.5891 |
| 50 | 105.67 | 1.06 | 37.72 | 0.38 | 2.8015 | 0.9464 | 2.6513 |
| 60 | 119.89 | 1.20 | 53.15 | 0.53 | 2.2559 | 0.8341 | 1.8816 |
| 70 | 125.97 | 1.26 | 72.64 | 0.73 | 1.7341 | 0.7939 | 1.3767 |
| 80 | 121.98 | 1.22 | 89.26 | 0.89 | 1.3666 | 0.8198 | 1.1203 |
| 90 | 110.95 | 1.11 | 100.82 | 1.01 | 1.1005 | 0.9013 | 0.9919 |
| 100 | 100.00 | 1.00 | 100.40 | 1.00 | 0.9961 | 1.0000 | 0.9961 |

TABLE 3

Residue

| Total Remaining Residue Volume % | % Marker A | Marker A ppm | % Marker B | Marker B ppm | Ratio A/B | Marker A Correction Factor | Marker B Correction Factor |
|---|---|---|---|---|---|---|---|
| 100 | 100.00 | 1.00 | 100.00 | 1.00 | 1.0000 | 1.0000 | 1.0000 |
| 90 | 103.89 | 1.04 | 110.13 | 1.10 | 0.9433 | 0.9625 | 0.9080 |
| 80 | 107.00 | 1.07 | 121.40 | 1.21 | 0.8814 | 0.9346 | 0.8237 |
| 70 | 108.38 | 1.08 | 134.26 | 1.34 | 0.8072 | 0.9227 | 0.7448 |
| 60 | 105.73 | 1.06 | 148.75 | 1.49 | 0.7108 | 0.9458 | 0.6723 |
| 50 | 94.33 | 0.94 | 163.07 | 1.63 | 0.5784 | 1.0601 | 0.6132 |
| 40 | 70.15 | 0.70 | 171.27 | 1.71 | 0.4096 | 1.4255 | 0.5839 |
| 30 | 39.40 | 0.39 | 165.16 | 1.65 | 0.2386 | 2.5379 | 0.6055 |
| 20 | 12.07 | 0.12 | 144.94 | 1.45 | 0.0833 | 8.2850 | 0.6899 |
| 10 | 1.41 | 0.01 | 96.59 | 0.97 | 0.0146 | 70.9220 | 1.0353 |
| 0 | 0.00 | 0.00 | 0.00 | 0.00 | 0.0000 | 0.0000 | 0.0000 |

It can be seen from Tables 2 and 3 above and plots in FIGS. 3 and 5, that there is always an excess of marker A in the distillate and there is always an excess of marker B in the residue. Therefore, if a sample is measured and it contains a significant increase in Marker A above normal analytical precision, we can deem this sample to have been distilled and the resultant product being measured is the resulting distillate from the distillation. Conversely, if the sample contains a significant increase in marker B then sample has been distilled and the resulting product being measured is the remaining distillation residue.

EXAMPLE 2

50 ml of the marked diesel fuel used in Example 1 (containing Marker A and Marker B, each at 1 ppmv) was mixed with 50 ml of used lubricating oil (ULO) which had an initial boiling temperature of 283° C. The resulting mixture was then subjected to atmospheric distillation to a temperature of 270° C. using a modified ASTM D-86 protocol. The volume of distillate recovered was 27 ml. Samples of un-distilled mixture, distillate, and Residue were analysed for the presence of marker. Results are tabulated in Table 4 below.

The concentration is shown as measured %, representing the volume of the marked diesel calculated to be in the sample using the measured concentration of the marker. This is calculated from the relationship (measured concentration of marker in sample/concentration of marker in marked diesel)*100%. Using the marker ratio NB found by analysis, the correction factor is obtained using the interpolated curves in FIG. 4 (for the distillate) and FIG. 6 (for the residue). The correction factor was then multiplied by the measured % to provide a corrected concentration of each marker in the sample. The "Reported % diesel in sample" column in Table 4 is the content of the marked diesel that is calculated to be present in the sample, calculated using an average of the corrected ppm of marker A and marker B. The reported value is calculated from: (corrected measured concentration of marker/concentration of marker in original marked product)*100) %.

TABLE 4

| Sample | Measured % A | Measured % B | Ratio A/B | Correction Factor A | Correction Factor B | Corrected % A | Corrected % B | Reported % diesel in sample | Theoretical % diesel in sample |
|---|---|---|---|---|---|---|---|---|---|
| Un-distilled | 49.7 | 51.3 | 0.9688 | 1.000 | 1.000 | 49.7 | 51.3 | 50.5 | 50 |
| Distillate | 97.9 | 38.2 | 2.5628 | 1.035 | 2.677 | 101.3 | 102.3 | 101.8 | 100 |
| Residue | 114 | 53.8 | 0.2119 | 2.749 | 0.638 | 31.3 | 34.3 | 32.8 | 31.5 |

The "theoretical % diesel in sample" column in Table 4 is the content of the marked diesel that would be present in the sample, calculated from knowledge of the amount of distillate distilled. For example, based on the IBP of the ULO, no ULO should distil over at 270° C. so the distillate (diesel lights) derives 100% from the original marked diesel. Since 27 ml was distilled from the original 50 mls marked diesel, 23 ml diesel (diesel heavies) remains in the residue fraction together with the 50 ml ULO. Therefore, the composition of original diesel remaining in the final product is (23/(23+50)*100)%.

Although the dilution of the product could be obtained only from measuring one of the markers, using the corrected concentration from both of the markers, for example as an average concentration may provide a means of compensating for measurement errors. It can be seen from Table 4 that the calculation of corrected concentration gives different values for marker A and marker B, when they were added to the diesel at the same concentration (1 ppm of each). An average of the corrected concentrations for A and B were used to calculate the reported values in Table 4.

The invention claimed is:

1. A method of marking a product having a distillation range and identifying the marked product in an unknown sample, comprising
    adding to said product a first marker, a second marker and optionally one or more further markers, each marker having a distillation range including a minimum boiling point (Min BP), a maximum boiling point (Max BP) and a maximum distillation boiling point (Max DBP) which is the temperature at which the maximum volume of the marker distils, each marker having a different distillation range from each other marker, and at least one marker having a Max DBP which is within the distillation range of the product, wherein the first marker has a distillation range in the marked product which extends over the whole of the product distillation range;
    analysing said unknown sample by an analytical method capable of providing a response which is proportional to the quantity of marker found in the unknown sample to identify whether said first marker, said second marker or a said further marker is present in said unknown sample;
    calculating a response ratio of the first and second markers in the unknown sample, to each other; and
    comparing the response ratio of the first and second markers in the unknown sample with a response ratio of the same markers in a reference sample to determine whether the unknown sample contains the known marked product or a distilled fraction or a residue fraction thereof.

2. The method as claimed in claim 1, wherein the marker distillation ranges of at least two markers overlap each other, and the respective Max DBPs of said at least two markers are different.

3. The method as claimed in claim 1, wherein the second marker has a distillation range in the marked product which extends over a portion of the distillation range over which at least 50% of the distillate fraction volume distils.

4. The method as claimed in claim 1, wherein the second marker has a distillation range in the marked product which extends over a portion of the distillation range over which at least 50% of the distillation residue fraction volume remains.

5. The method as claimed in claim 1, wherein the second marker has a marker distillation range which overlaps the initial boiling point (IBP} of the product.

6. The method as claimed in claim 1, wherein the second marker has a marker distillation range which overlaps the final boiling point (FBP} of the product.

7. The method as claimed in claim 1, wherein said first marker has a lower maximum distillation boiling point (Max DBP) than the max DBP of said second marker and wherein the response ratio of the first marker to the second marker in said unknown sample is greater than the response ratio of the first marker to the second marker in said reference sample, and further comprising determining that the unknown sample contains a distillate fraction of the marked product.

8. The method as claimed in claim 1, wherein said first marker has a lower maximum distillation boiling point (Max DBP) than the max DBP of said second marker and wherein the response ratio of the first marker to the second marker in said unknown sample is less than the response ratio of the first marker to the second marker in said reference sample, and further comprising determining that the unknown sample contains a residue fraction of the marked product.

9. The method as claimed in claim 1, further comprising calculating a correction factor for said first marker by a method comprising:
   a. distilling a reference sample representing the known marked product containing a known concentration of said first marker to obtain at least two reference distillate fractions each of known distillation volume % and at least two reference residue fractions each of known residue volume %;
   b. each of said distillate and residue fractions to determine the response of said first marker in each fraction;
   c. determining the correction factor (CF) for said first marker in each fraction from:

$$CF = \frac{\text{response of first marker in fraction}}{\text{response of first marker in reference sample}}.$$

10. The method as claimed in claim 9, further comprising calculating a correction factor for said second marker by a method comprising:
   a. distilling a reference sample representing the known marked product containing a known concentration of said second marker to obtain at least two reference distillate fractions each of known distillation volume % and at least two reference residue fractions each of known residue volume %;
   b. each of said distillate and residue fractions to determine the response of said second marker in each fraction;
   c. determining the correction factor (CF) for said second marker in each fraction from:

$$CF = \frac{\text{response of second marker in fraction}}{\text{response of second marker in reference sample}}.$$

11. The method as claimed in claim 9, further comprising interpolating said calculated correction factors over the range of said distillate volume fractions.

12. The method as claimed in claim 9, further comprising interpolating said calculated correction factors over the range of said residue volume fractions.

13. The method as claimed in claim 9, further comprising correlating said correction factor for the first and/or the second marker with the response ratio of said first marker to said second marker at each distillate or residue volume fraction.

14. The method as claimed in claim 13, comprising comparing the response ratio of the first marker to the second marker in the unknown sample to the correlation of the correction factor for the first and/or the second marker with the response ratio of said first marker to said second marker in the reference sample to determine the correction factor to use to calculate the proportion of a distillate or a residue fraction of said marked product present in said unknown sample.

15. The method as claimed in claim 14, comprising calculating the proportion of a distillate or a residue fraction of said marked product present in said unknown sample.

* * * * *